United States Patent [19]

Shirakami et al.

[11] Patent Number: 4,887,614

[45] Date of Patent: Dec. 19, 1989

[54] MEDICAL ELECTRODE DEVICE

[75] Inventors: Toshiharu Shirakami, Hino; Akira Sogawa, Tokyo, both of Japan

[73] Assignee: Kureha Kagaku Kogyo Kabushiki Kaisha, Tokyo, Japan

[21] Appl. No.: 339,875

[22] Filed: Apr. 18, 1989

Related U.S. Application Data

[63] Continuation of Ser. No. 158,133, Feb. 17, 1988, abandoned, which is a continuation of Ser. No. 918,627, Oct. 14, 1986, abandoned, which is a continuation of Ser. No. 645,105, Aug. 28, 1984, abandoned.

[30] Foreign Application Priority Data

Sep. 5, 1983 [JP] Japan ................... 58-163046

[51] Int. Cl.⁴ ............................................. A61N 1/06
[52] U.S. Cl. ........................... 128/798; 128/804; 128/402
[58] Field of Search .............. 128/804, 399–403, 128/802, 639, 644, 798; 600/9–10, 15

[56] References Cited

U.S. PATENT DOCUMENTS

| 254,265 | 2/1882 | Bone | 128/400 |
|---|---|---|---|
| 1,637,829 | 8/1927 | Lurie | 128/802 |
| 1,853,814 | 4/1932 | Huth | 128/798 |
| 1,973,387 | 9/1934 | Neymann et al. | 128/798 |
| 2,726,658 | 12/1955 | Chessey | 128/402 X |
| 3,561,435 | 2/1971 | Nicholson | 128/402 X |
| 3,610,323 | 10/1971 | Troyer | 128/402 X |
| 3,662,757 | 5/1972 | Blackett | 128/798 |
| 3,888,259 | 6/1975 | Miley | 128/400 |
| 4,118,946 | 10/1978 | Tubin | 128/400 X |
| 4,121,582 | 10/1978 | Remiro | 128/402 X |
| 4,140,130 | 2/1979 | Storm, III | 128/400 X |
| 4,149,541 | 4/1979 | Gammons et al. | 128/400 |
| 4,154,245 | 5/1979 | Daily | 128/401 X |
| 4,259,961 | 4/1981 | Hood, III | 128/400 |
| 4,290,435 | 9/1981 | Waggott | 128/800 |
| 4,384,582 | 5/1983 | Watt | 128/798 X |
| 4,422,461 | 12/1983 | Glumac | 128/798 |
| 4,509,535 | 4/1985 | Bryan | 128/798 |
| 4,662,383 | 5/1987 | Sogawa et al. | 128/784 |
| 4,767,258 | 6/1987 | Inokuchi et al. | 128/804 |

FOREIGN PATENT DOCUMENTS

| 105677 | 4/1984 | European Pat. Off. . | |
| 2263727 | 7/1974 | Fed. Rep. of Germany | 128/802 |
| 2407559 | 8/1975 | Fed. Rep. of Germany . | |
| 2727822 | 1/1979 | Fed. Rep. of Germany | 128/802 |
| 2156471 | 10/1971 | France . | |
| 2342082 | 2/1976 | France . | |
| 2288531 | 5/1976 | France | 128/798 |
| 81/03616 | 12/1981 | World Int. Prop. O. . | |

Primary Examiner—Angela D. Sykes
Attorney, Agent, or Firm—Oblon, Spivak, McClelland, Maier & Neustadt

[57] ABSTRACT

A medical electrode device comprises a flexible bag-like member which is formed on the side in direct contact with a living body and to and from which is charged and discharged a cooling medium, and a flexible electrode secured to the bag-like member, wherein an inner surface of the flexible bag-like member is at least partially joined to the other opposing inner surface of the bag-like member to each other so as to form a partitioned flow channel for the cooling medium in the inside of the bag-like member. The medical electrode device, when applied to the surface of a living body with a small radius of curvature, can be in an intimate contact with the living body without disturbing the distribution of the electric field, can attain a satisfactory cooling effect due to the use of a direct cooling system and the uniform flow distribution of water through the partitioned flow channel, and can perform efficient warming of the targeted lesion in the living body.

9 Claims, 9 Drawing Sheets

MEDICAL ELECTRODE DEVICE

This application is a continuation of application Ser. No. 07/158,133, filed on Feb. 17, 1988, now abandoned, which is a continuation of application Ser. No. 06/918,627, filed on Oct. 14, 1986, now abandoned, which is a continuation of application Ser. No. 06/645,105, filed on Aug. 28, 1984, now abandoned.

FIELD OF THE INVENTION

This invention concerns a medical electrode device and, more specifically, it relates to an electrode device of a warming apparatus for a living body using electromagnetic waves, particularly, a warming apparatus capable of being used for a thermotherapy (or hyperthermia therapy) of tumors.

BACKGROUND OF THE INVENTION

Hyperthermia therapy (i.e., warming cancerous lesions utilizing the fact that cancer cells are more heat sensitive than normal cells) has been well known. The known methods of warming the lesions includes using electromagnetic waves. In using electromagnetic waves, the heat generated upon absorption of the electromagnetic waves applied to a living body is utilized for warming the living body, and there have been many reports in recent years of the effects thereof against malignant tumors.

Referring to FIGS. 1 and 2 an example of thermotherapy using high frequency warming will be explained. A region 3 of a living body 1 including a lesion 2 to be warmed as the target is put between two opposing plate-electrodes 4 and 5. High frequency current is caused to flow from a high frequency power source 6 across the plate electrodes 4 and 5 placed on the front and rear sides of the living body 1.

The degree of absorption of the electromagnetic waves is different depending on the tissues of the living body. For example, in the case of ultra high frequency waves, the absorption mainly occurs in the skin and muscle layers. On the other hand, high frequency waves are mostly absorbed in the fatty layer. Accordingly, when thermotherapy is carried out by warming the targeted lesion in the living body to a desired temperature by the pair of the electrodes disposed outside of the body, localized heating occurs near the surface of the living body to worry the patient with the undesired sense of heat and even cause a risk of burn at the surface layer tissue.

In order to avoid the feeling of heat and the risk of a burn to the surface layer tissue, it is necessary to cool the localized excessively heated portion. Accordingly, an electrode device of a structure provided with cooling means on the side of the plate electrode in contact with the living body as shown in FIG. 3 and FIG. 4 has been employed so far.

In FIG. 3 and FIG. 4, an electrode 7 made of a circular copper plate is connected by way of a lead wire 8 to a high frequency source (not shown). On the side A of the electrode 7 in contact with a living body, a spiral silicone rubber tube 9 is secured. A polymeric bag 10 in a rectangular configuration encloses the electrode 7 and the tube 9. Cooling water 11 is sealed within the polymeric bag 10 with an aim of cooling the localized excessively heated portion of the living body. The temperature of the cooling water 11 in the bag 10 is controlled by cooling water 12 circulating through the silicone rubber tube 9.

However, the conventional electrode device having the foregoing constitution involves various drawbacks upon actual use such as described below:

(1) Since the electrode device lacks in flexibility, it can not be in an intimate contact with the living body. Particularly, when it is applied to the surface of a living body with a small radius of curvature, an air gap is formed between the living body and the surface of the bag 10, which disturbs the distribution of the electric field.
(2) Since the cooling with the cooling water 12 is performed indirectly by means of the cooling water 11, the cooling efficiency is poor.
(3) Since there is no partitioning structure in the bag 10 for containing the cooling water, water flow may be deviated in the bag, causing uneven cooling.

OBJECT OF THE INVENTION

This invention has been accomplished in view of the foregoing. The principal object of the invention is to provide a medical electrode device capable of cooling the excessively heated portion of a living body uniformly and with high efficiency, as well as capable of warming the targeted lesion with the living body in high efficiency.

SUMMARY OF THE INVENTION

In accordance with this invention, a foregoing object can be attained by the medical electrode device comprising a flexible bag-like member which is formed on the side in direct contact with a living body and to and from which is charged and discharged a cooling medium. A flexible electrode is secured to the bag-like member. An inner surface of the flexible bag-like member is at least partially joined to the other opposing inner surface of the bag-like member to each other so as to form a partitioned flow channel for the cooling medium in the inside of the bag-like member.

In the medical electrode device according to this invention, since the flow channel for the cooling medium flowing through the inside of the bag-like member which is in direct contact at the outer surface thereof with the living body is formed as a single channel or a plurality of channels in one optional direction, there is no risk that the flow of the cooling medium localizes within the bag-like member. Moreover, since a direct cooling system is employed in which the cooling medium is in contact with the living body only by way of a flexible sheet-like material, cooling exchange between the heat medium and the excessively heated portion of the living body can be performed efficiently and uniformly.

Further, since the side of the electrode device in contact with the surface of the living body is formed from a flexible sheet-like material, the sheet-like material can be expanded by supplying the cooling medium to the bag-like member under pressure to ensure a satisfactory close contact with the living body.

Furthermore, in the medical electrode device according to this invention, since an inner surface of the flexible sheet-like material situated on the side of the flexible bag-like member in direct contact with the living body is at least partially joined with the other opposing inner surface of the bag-like member, the device can be bent with ease at the joined portion so as to profile the surface configuration of the living body.

It is preferred that the medical electrode device according to this invention has a flexibility in view of its purpose of use. Accordingly, the electrode device is suitably constituted with relatively thin members, but there are no particular restrictions for the material and the shape thereof.

The elastic material for the sheet-like material of the bag-like member on the side in contact with the living body can include, for example, natural or synthetic rubber such as butadiene rubber, silicone rubber or ethylene vinyl acetate copolymer. The bag-like member may be entirely formed from such elastic material. Instead of an elastic material, a flexible material (including, for example, polyvinyl chloride, silicone resin and nylon), sheets made of such synthetic resins, or sheets prepared by knitting the fibers of such synthetic resins may also be used. The electrode usable herein includes, for example, a single sheet of metal foil such as made of copper, aluminum and silver, a plurality of such metal foils connected electrically, or braided products made of the abovementioned metals. While the configuration of the electrode has no particular restrictions, a rectangular shape is preferred more than the circular shape in view of the distribution density of the electric field when it is used in combination with a cylindrical endotract electrode as described later.

DESCRIPTION OF THE ACCOMPANYING DRAWINGS

This invention is to be described in more details referring to the accompanying drawings, by which the foregoing and other objects, as well as the features of this invention will be made clearer:

Figure 5:
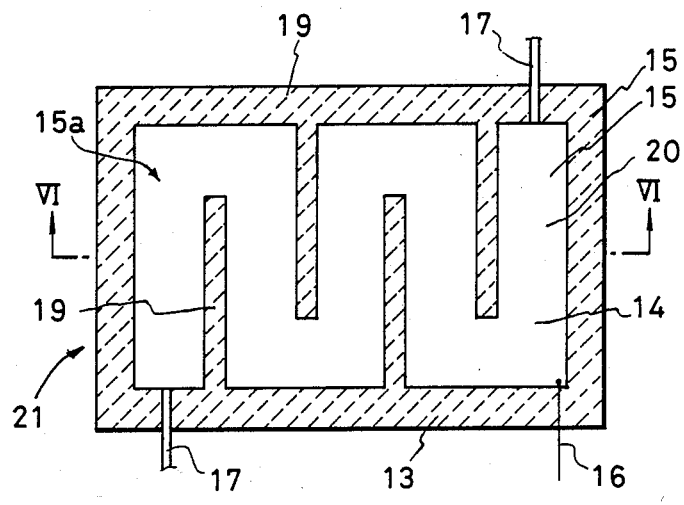
Figure 6:
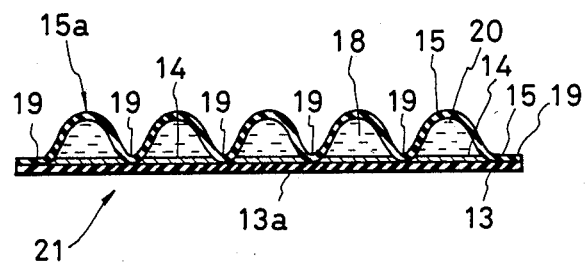
Figure 7:
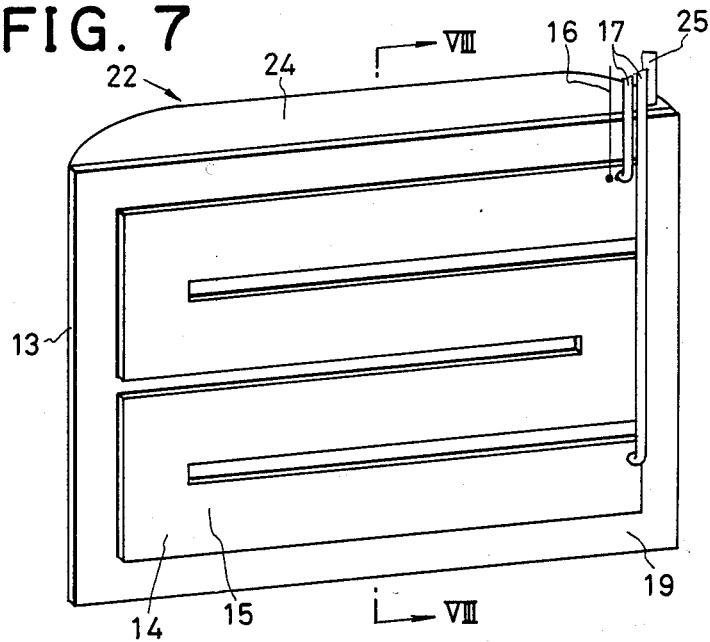
Figure 8:
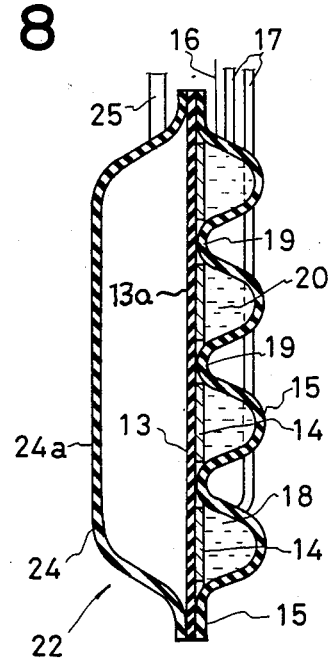
Figure 9:
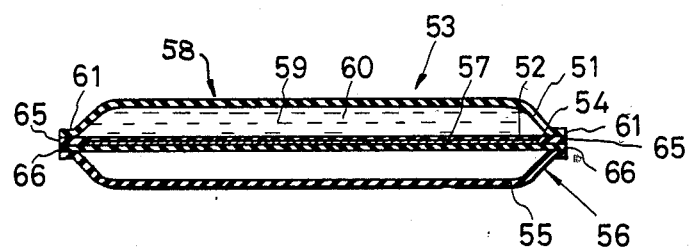

FIG. 5 is an explanatory view for the medical electrode device as a preferred embodiment according to this invention, FIG. 6 is an explanatory cross sectional view taken along line VI—VI in FIG. 5, FIG. 7 is an explanatory view for the medical electrode device as another preferred embodiment according to this invention, FIG. 8 is an explanatory cross sectional view taken along line VIII—VIII in FIG. 7, FIG. 9 is an explanatory cross sectional view of the medical electrode device as a further preferred embodiment according to this invention.

Figure 13:
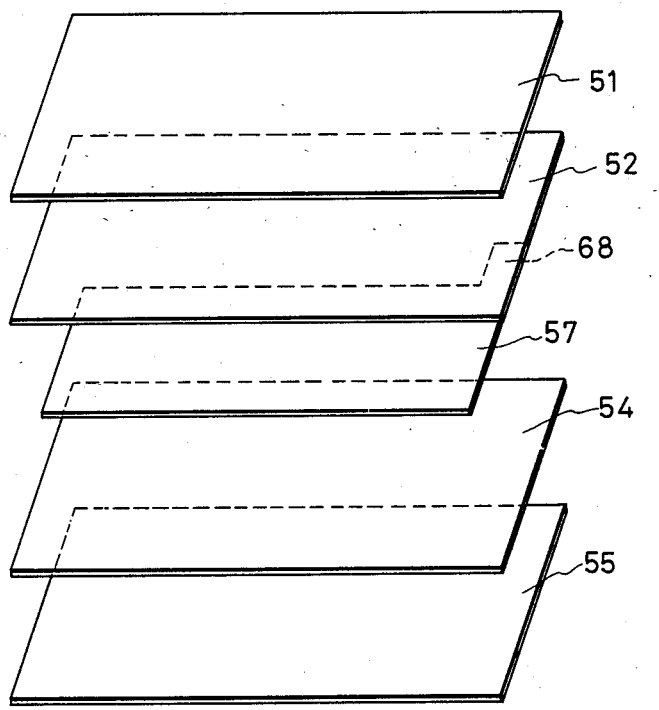
Figure 10:
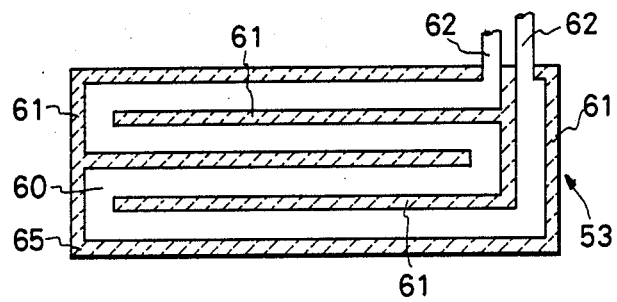
Figure 11:
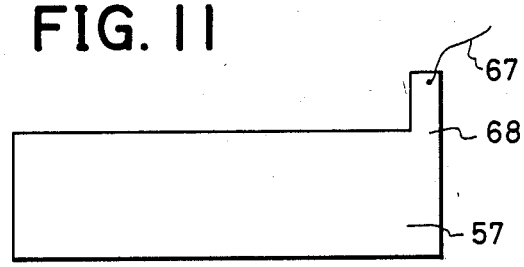
Figure 12:
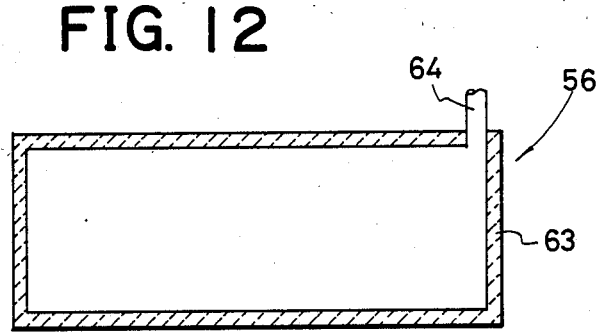
Figure 14:
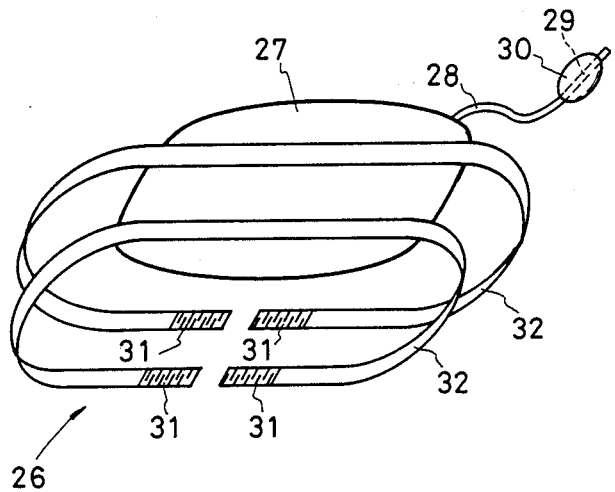
Figure 15:
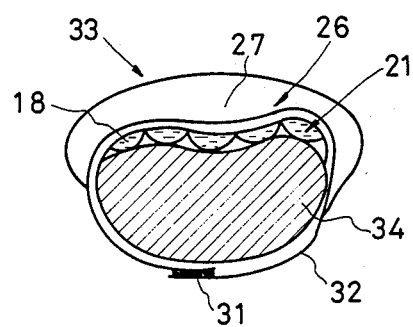
Figure 16:
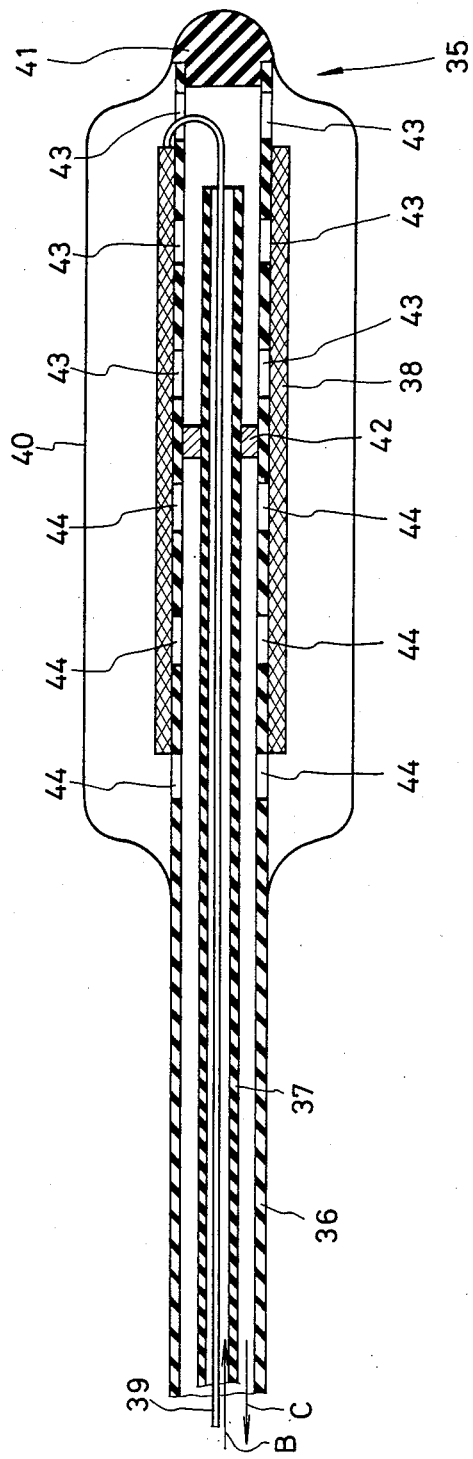
Figure 17:
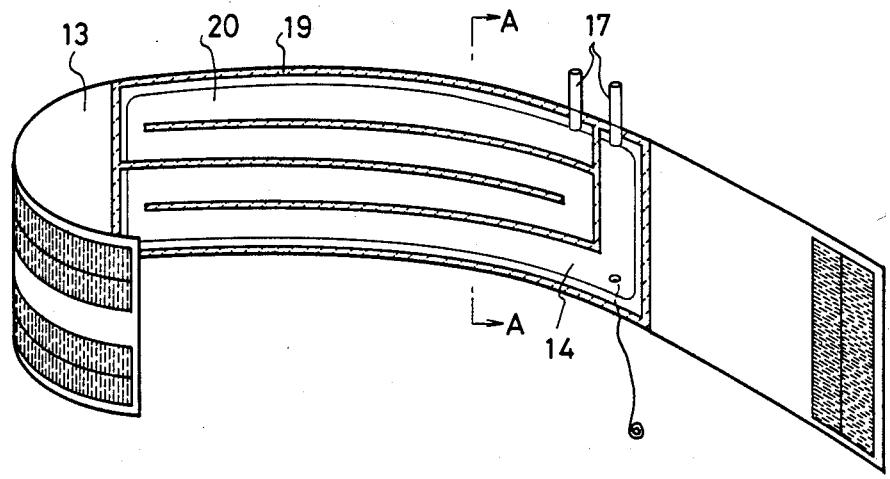
Figure 18:
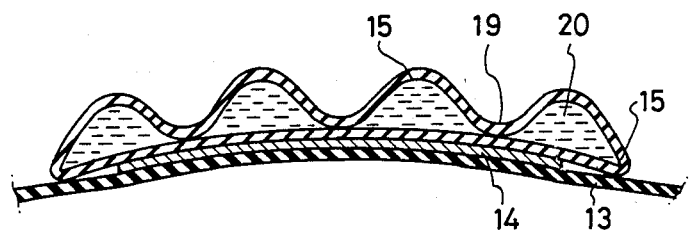

FIG. 10 is an explanatory view for a bag-like member in the medical electrode device shown in FIG. 9, FIG. 11 is an explanatory view for the electrode of the medical electrode device shown in FIG. 9, FIG. 12 is an explanatory view for the presser member of the medical electrode device shown in FIG. 9, FIG. 13 is an explanatory view for the constituent members of the medical electrode device shown in FIG. 9, FIG. 14 is an explanatory view for the fixing tool of a preferred embodiment for use in the electrode applicator according to this invention, FIG. 15 is and explanatory view of the electrode applicator as a preferred embodiment according to this invention, FIG. 16 is an explanatory view for one embodiment of the endotract heating electrode that can be used together with the medical electrode device according to this invention, FIG. 17 is an explanatory view for the medical electrode device as another preferred embodiment according to this invention, and FIG. 18 is an explanatory cross sectional view taken along line A—A in FIG. 17.

DESCRIPTION OF THE PREFERRED EMBODIMENTS

FIG. 5 and FIG. 6 illustrate one embodiment of the medical electrode device according to this invention. In FIG. 5 and FIG. 6, a substrate 13 is made of a nylon cloth coated with a silicone resin. There are also shown a foil electrode 14 made of a copper foil, a stretchable silicone rubber sheet 15, a lead wire 16 to be connected at one end to a high frequency power source (not shown), and silicone tubes 17 as charge and discharge pipes for a cooling medium 18. The substrate 13 and the stretchable silicone rubber sheet 15 are joined at a portion 19 shown by the hatched line in order to form a cooling medium flow channel 20 in one direction between the silicone tubes 17, 17.

FIG. 6 is a cross sectional view taken along line VI—VI in FIG. 5 showing the state where the cooling medium 18 is being supplied under pressure. In FIG. 6, the upper portion of the device is brought into a close contact with the surface of the living body. In the above embodiment, the bag-like member 15a is constituted from the stretchable silicone rubber sheet 15 and the substrate fiber sheet 13.

The electrode device 21 in this embodiment can be in an intimate contact with the living body due to the interaction between the fixing tool as described later and the expansion of the stretchable silicone rubber sheet 15.

In the medical electrode device 21, the foil electrode 14 may have the same rectangular shape as that of the substrate 13, instead of being formed in the same planar shape as that of the heat medium flow channel 20. Moreover, the foil electrode 14 may be secured to the substrate 13, and the stretchable silicone rubber sheet 15 may be secured to the portion 19 on the foil electrode 14. It is, however, desirable to form the foil electrode 14 as shown in FIG. 5 and FIG. 6. Further, the foil electrode 14 may be placed on the rear face 13a of the substrate 13. In this case, the foil electrode 14 may be made detachable from the bag-like member 15a. The foil electrode 14 may be applied with an insulative coating.

In FIG. 5 and FIG. 6, while the flow channel 20 for the cooling medium (for example, cooling water) is shown as a single serpentine or zig-zag flow channel, it may comprise a composite channel in which a plurality of channels are disposed and branched, crossed, or extended in parallel separately.

The cooling medium channel 20 of the serpentine type may be extended in a zig-zag manner not only vertically as shown in FIG. 5 but also right- and leftwardly in FIG. 5.

The medical electrode 21 according to this invention can be manufactured, but not limitatively, by the following procedures.

(1) Each of the members is cut into an optional size, for example, of a rectangular configuration.

(2) In order to form the cooling water flow channel and secure the joining portion 19 between the substrate 13 and the stretchable silicone rubber sheet 15, a rectangular copper foil backed with paper sheet is partially cut out to form the foil electrode 14, to which the lead wire 16 is soldered.

(3) Silicone type adhesives are coated and extended uniformly over the surface of the substrate 13 on the side coated with the silicone.

(4) The copper foil electrode 14 as prepared in (3) above is disposed on the adhesive-coated surface and then attached with fixing tape.

(5) The silicone tubes 17, 17 serving as the charge and discharge pipes are placed on predetermined positions and a sufficient amount of adhesives is applied at the attaching portion of the silicone tubes 17, 17 and the leading portion of the lead wire 16 so as not to result in leakages.

(6) Then, the stretchable rubber silicone sheet 15 is covered thereover from above so as not to produce wrinkles and left as it is while pressing the bonded portion 19 (particularly at the periphery).

FIG. 7 and FIG. 8 show a medical electrode device 22 as another embodiment according to this invention. In the medical electrode device 22, a sheet 24a similar to the substrate 13 of the medical electrode device 21 previously shown in FIG. 5 and FIG. 6 is attached at the rear face 13a of the substrate 13 of the medical electrode device so as to define a bag-like presser member 24 for charging pressurized air. The similar components in the medical electrode device 22 to those in the medical electrode device 21 carry the same reference numerals. A charge and discharge pipe 25 is attached to the presser member 24.

Instead of disposing the electrode to the inside of the bag-like member, it may be disposed outside of the bag-like member as shown below.

FIG. 9 shows a medical electrode device 53, in which an electrode sheet 57 is disposed between a bag-like member 58 defined with films 51, 52 and a presser member 56 defined with films 54, 55.

The film 51 is a sheet similar to the stretchable silicone rubber sheet 15, and the film 52 is a sheet similar to the substrate 13. The films 51 and 52 are firmly secured to each other in a liquid or gas tight manner at the portion 61 shown by the hatched line in FIG. 10 so as to form the cooling medium flow channel 60 for the cooling medium 59. Charge and discharge tubes 62, 62 are attached for the cooling medium 59.

The films 54, 55 are sheets similar to the substrate 13 or the sheet 24a. They are secured to each other in a gas tight manner at a portion 63 shown by the hatched line in FIG. 12 so as to form the bag-like presser member 56 for containing the pressurized gas. A charge and discharge pipe 64 for the pressurized gas communicates with the interior of the bag-like pressure member.

The electrode sheet 57 between the film 52 (which is a part of the bag-like member 58 and the film 54 (which is a part of the presser member 56) is rectangular in shape and is somewhat smaller than the films 51, 52, 54, 55. The electrode sheet 57 is put between the films 52 and 54, and the films 52, 54 are secured at their peripheral portions 65, 66. The electrode sheet 57 may be secured directly on the entire surface thereof to the films 52, 54. In FIG. 11, a lead wire 67 for the electrode sheet 57 and an electrode projection 68 for attaching the lead wire 67 are shown.

The medical electrode device 53 having the foregoing constitution can be manufactured by overlaying the films 51, 52, electrode sheet 57 and the films 54, 55 as shown in FIG. 13 and applying heat sealing from above by utilizing heat or pressure by an appropriate sheet laminating means.

The medical electrode device 53 may be manufactured by forming the bag-like member 58 from the films 51, 52, while forming the presser member 56 from the films 54, 55, thereafter, placing the electrode sheet 57 between the thus formed bag-like member 58 and the presser member 53, and then securing the bag-like member 58 and the pressing member 56 to each other.

If desired, adhesives may be use for securing the films to each other.

In the case where the pressing member 56 is not formed integrally with the bag-like member 58, use of the film 55 may be saved. Further, in the case where the upper face of the electrode sheet 57 is secured to the lower face of the film 52, the film 54 may be saved.

The medical electrode device according to this invention, if removed with the electrode, can be used as a fluid container for cooling and warming the lesion.

The sheet 15 or the film 51 of the device on the side contacting the living body may be corrugated instead of flat where the sheet is only required to be flexible.

The medical electrode device according to this invention has a flexibility. Accordingly, it can be placed on and kept in close contact with various portions of the living body. However, such an intimate contact can be kept more firmly by the combined use of a fixing tool 26 shown in FIG. 14.

In FIG. 14, a hollow presser member 27 is made of a expansible and shrinkable material such as an elastic polymeric material. The presser member 27 is connected to a pump 30 by a charge and discharge tube 28 made of flexible polymeric material or the like and a charge and discharge valve mechanism 29. The presser member 27 is further attached with fixing belts 32, 32 comprising joining means 31 such as magic tapes. The fixing belts 32 serve to exert the expanding force of the presser member 27 in the direction of closely contacting the medical electrode device and the living body, but it is not necessarily that they be integrated with the presser member 27. There are also no particular restrictions for their shape and material.

FIG. 15 shows the state of using a medical electrode applicator 33 including the fixing tool 26 having the presser member 27 and the fixing belts 32, and the medical electrode device 21. As shown in FIG. 15, the medical electrode device 21 is placed on the outer circumferential surface of a living body to be warmed 34, the presser member 27 is placed thereover, and they are fixed with the fixing belts 32. Then, the cooling medium 18 is introduced into the medical electrode device 21. Then, while observing the flow rate of the cooling medium 18, the presser member 27 is expanded by the pump 30 having the charge and discharge valve mechanism 29 to secure a close contact between the medical electrode device 21 and the living body 34. In this case, care should be taken so that the presser member 27 does not expand excessively, since this hinders the flow of the cooling medium 18 passing through the inside of the medical electrode device 22. The electrode applicator 33 may be constituted, instead of from the presser member 27 and the medical electrode device 21, by using the medical electrode device 22 or the medical electrode device 53 in which the presser member is integrated with the substrate, thereby constituting the electrode applicator with the medical electrode device 22 or 53 and the fixing belt 32. Further, the electrode applicator 33 may also be constituted by integrally mounting the fixing belt 32 to the end of the medical electrode device 22 or 53 on the side of the presser member 24 or 56.

Figure 1:
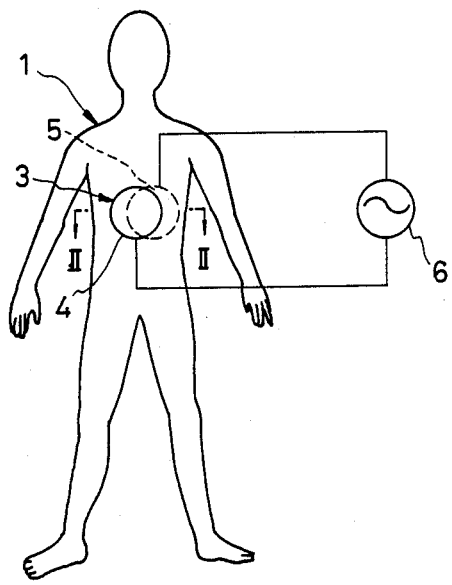
FIG. 1 is an explanatory view for a medical heating device.
Figure 2:
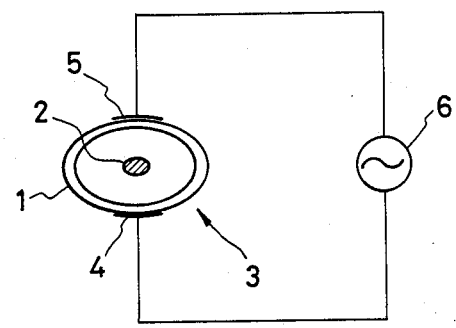
FIG. 2 is an explanatory cross sectional view taken along line II—II in FIG. 1.
Figure 3:
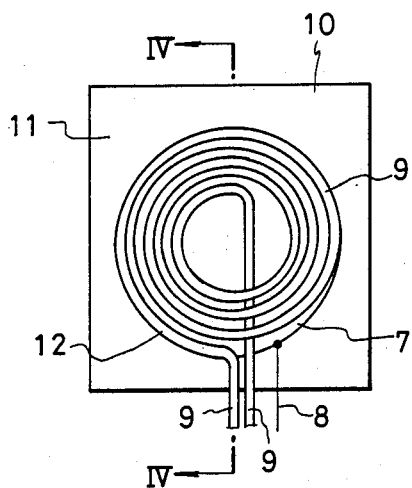
FIG. 3 is an explanatory view for a conventional medical electrode device.
Figure 4:
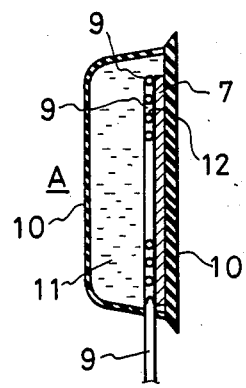
FIG. 4 is an explanatory cross sectional view taken along line IV—IV in FIG. 3.

As described above, the medical electrode device according to this invention can be used solely or in combination with the fixing tool as described above, as one or both of the pair of electrodes in the electromagnetic warming device as shown in FIG. 1 and FIG. 2.

In this case, two electrode devices constituting two plate electrodes 4, 5 may be connected with a single substrate 13.

The medical electrode device according to this invention may be employed as the electrode disposed outside of the body while being in combination with another electrode inserted and disposed in the endotract.

As the electrode disposed in the inside of the endotract, an endotract heating electrode as shown in FIG. 16 previously proposed by the present inventors (Japanese patent application No. 9658/1983) may be used.

In the endotract heating electrode 35 shown in FIG. 16, are shown flexible tubes 36, 37, a flexible cylindrical electrode 38, a lead wire 39, a bag-like member 40 made of elastic material, a cap 41, a seal member 42, and apertures 43 and 44. Referring briefly to the endotract heating electrode 35, after placing the electrode 35 from its rightmost end to the inside of the endotract, water or a cooling medium is caused to flow in the direction B. Then, the bag-like member 40 is expanded by the cooling medium flowing through the flexible tube 37 and the aperture 43. The circulating cooling medium, excess heat medium or heat medium discharged before taking out the electrode 35 is discharged passing through the aperture 44 and the flexible tube 36 in the direction C.

As a result of the clinical test leaving the endotract heating electrode 35 in the inside of the esophagus and by merely placing the medical heating electrode according to this invention on the chest of a patient lying on his back, it was confirmed that the cooling efficiency was satisfactory and the endotract portion could be warmed sufficiently.

FIG. 17 and FIG. 18 illustrate another embodiment of the medical electrode device according to this invention. In the FIG. 17 and FIG. 18, there are shown medical electrode devices which have the foil electrode 14 secured to the outer side of the flexible bag-like member. The substrate 13 is provided so as to cover the foil electrode 14. The substrate 13 is made of a nylon cloth coated with a vinyl chloride, and the fixing belts are provided on the opposite ends of the substrate 13. FIG. 18 is an explanatory cross sectional view taken along line A—A in FIG. 17 showing the state where the cooling medium is being supplied under pressure.

What is claimed is:

1. A medical electrode device for use in radio-frequency hyperthermia comprising:
    (a) a flexible bag-like member comprising:
        (i) an inner sheet-like member and
        (ii) an outer sheet-like member having a flat shape,
        (iii) an inner shape being defined between said inner and outer sheet-like members,
        (iv) said flexible bag-like member comprising at least first, second, and third partitioning portions forming a zig-zag passage in said inner space,
        (v) said first, second, and third partitioning portions each being formed by securing said inner sheet-like member to said outer sheet-like member,
        (vi) said inner sheet-like member and said outer sheet-like member making substantially only line contact with each other where they are secured to each other,
        (vii) said inner sheet-like member being adapted to be in direct contact with a living body during use of said medical electrode device,
        (viii) said first and second partitioning portions continuously extending in parallel to each other from a first peripheral edge of said bag-like member in the direction of a second peripheral edge opposite to said first peripheral edge,
        (ix) said third partitioning portion continuously extending between said first and second partitioning portions in parallel to said first and second partitioning portions from said second peripheral edge in the direction of said first peripheral edge,
        (x) said first, second, and third partitioning portions being substantially narrower than said zig-zag passage in width;
    (b) means for circulating a cooling medium through said zig-zag passage;
    (c) a flexible electrode secured closely onto said outer sheet-like member of said flexible bag-like member such that said flexible bag-like member is disposed between said flexible electrode and the living body during use of said medical electrode device; and
    (d) a fixing belt disposed behind said flexible electrode for uniformly pressing the medical electrode device against the living body so that said flexible electrode spaces substantially in parallel with the surface of the living body,
    wherein, upon introduction of the cooling medium into said zig-zag passage;
    (e) said outer sheet-like member maintains substantially a flat shape;
    (f) said inner sheet-like member inflates to form a corrugated shape; and
    (g) the corrugations in said inner sheet-like member touch each other on their sides and the inner surface of the corrugations is substantially continuous so as to make a uniform contact with an outer surface of said living body during use of said medical electrode device.

2. The medical electrode device according to claim 1, in which said inner sheet-like member is formed of film.

3. The medical electrode device according to claim 1, in which said inner sheet-like member is in a flat shape before the cooling medium is introduced into said zig-zag passage.

4. The medical electrode device according to claim 3, in which said inner sheet-like member comprises an elastic material.

5. The medical electrode device according to claim 3, in which said inner sheet-like member comprises a synthetic resin.

6. The medical electrode device according to claim 1, in which said inner sheet-like member is formed in a corrugated shape even before the cooling medium is introduced into said zig-zag passage.

7. The medical electrode device according to claim 6, in which said inner sheet-like member comprises an elastic material.

8. The medical electrode device according to claim 6, in which said inner sheet-like member comprises a synthetic resin.

9. The medical electrode device according to claim 1, in which said zig-zag passage is branched to form a composite passage.

* * * * *

UNITED STATES PATENT AND TRADEMARK OFFICE
CERTIFICATE OF CORRECTION

PATENT NO. :   4,887,614

DATED      :   December 19, 1989

INVENTOR(S):   TOSHIHARU SHIRAKAMI ET AL

Page 1 of 2

It is certified that error appears in the above-identified patent and that said Letters Patent is hereby corrected as shown below:

In column 2, line 28, change "with the living body in" to --in the living body with--;

In column 2, line 32 change "a foregoing" to --the foregoing--;

In column 2, line 33 change "the medical" to --a medical--;

In column 2, line 53 change "cooling exchange" to --heat exchange--;

In column 2, line 54 change "heat medium" to --cooling medium--;

In column 5, line 60 change "52( which" to --52 which--;

In column 7, line 67 change "inner shape" to --inner space--;

In column 2, line 6 change "lacks in flexibility" to --lacks flexibility--;

In column 4, line 1 change "and explanatory" to --an explanatory--;

In column 6, line 16 change "be use" to --be used--;

UNITED STATES PATENT AND TRADEMARK OFFICE
CERTIFICATE OF CORRECTION

PATENT NO. : 4,887,614
DATED : December 19, 1989
INVENTOR(S) : TOSHIHARU SHIRAKAMI ET AL It is certified that error appears in the above-identified patent and that said Letters Patent is hereby corrected as shown below:

In column 7, line 37 to 39 delete ", excess heat medium - out the electrod 35".

Signed and Sealed this

Twenty-fifth Day of June, 1991

Attest:

HARRY F. MANBECK, JR.

*Attesting Officer*

*Commissioner of Patents and Trademarks*